June 20, 1972 W. H. JESSEL, JR., ET AL Plant Pat. 3,215
CHRYSANTHEMUM PLANT
Filed Oct. 14, 1970
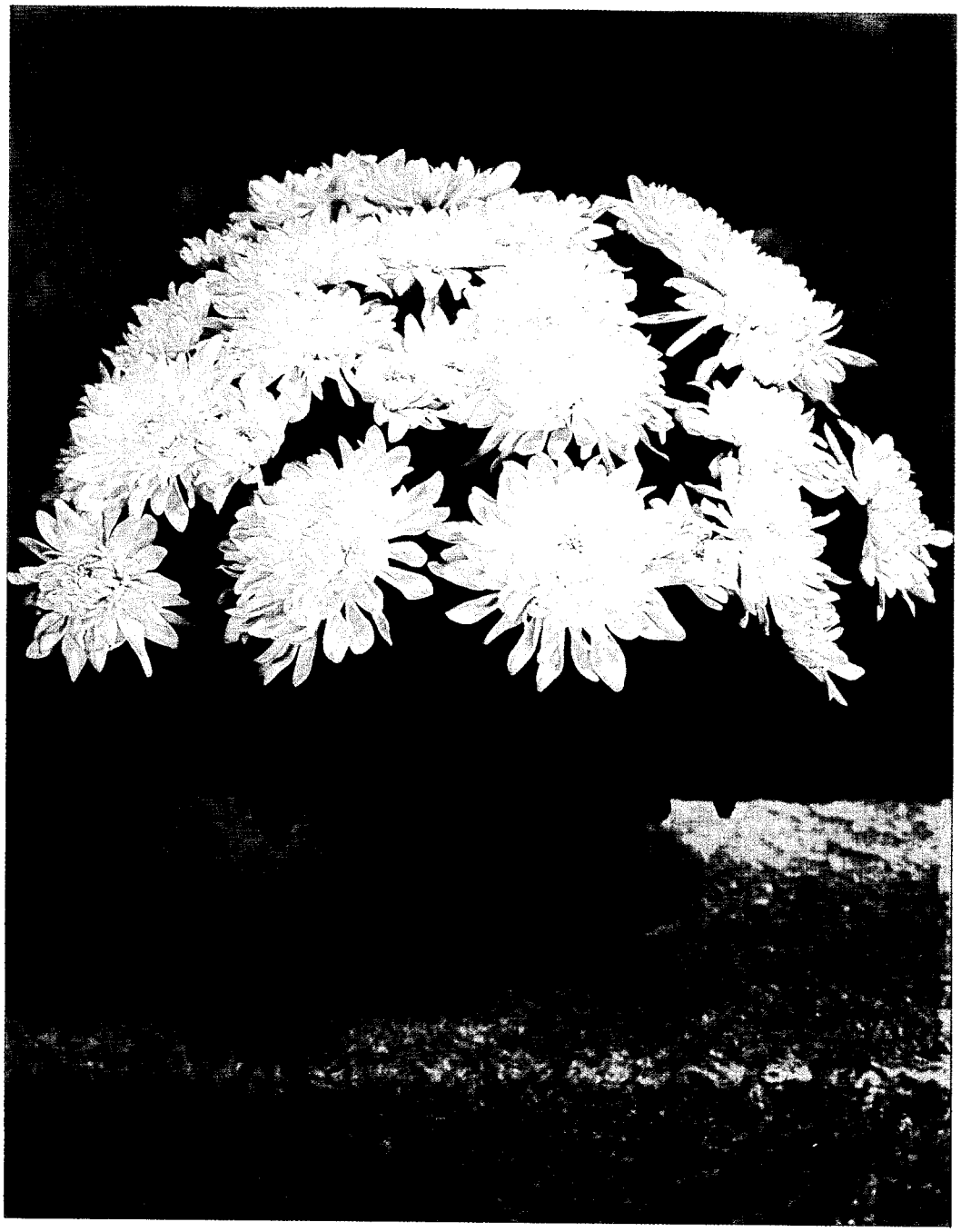
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,215

Patented June 20, 1972

3,215
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 14, 1970, Ser. No. 80,823
Int. Cl. A01h *5/00*
U.S. Cl. Plt.—77 1 Claim

The present invention comprises a new and distinct cultivar of chrysanthemum plant which is a seedling of #6591-2×#62966-1. Both parents are unnamed and unpatented and are identified for breeding purposes in this manner.

The new cultivar is similar in many respects to the commercially well-known, unpatented cultivar Neptune, one of the industry standards, having the same characteristics as Neptune of:

(1) Pure white flower color.
(2) Decorative type form.
(3) Uniform flowering response at high and low temperatures.

The new cultivar is distinguished from Neptune by the following characteristics:

(1) One inch to one and one half inches larger flowers.
(2) Petals approximately ¾″ wider.
(3) Less upright habit.
(4) Non-pinking of flower with a cool finish of 60° F. or less.
(5) A lighter colored foliage.
(6) Longer leaves by 1″.

(7) A flatter petal during high light, high temperature periods, with no longitudinal roll as the flower matures.
(8) Greater spread.
(9) One week later response.
(10) Three inches more vigor when given the same long day treatment.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, total vigor, and color may vary significantly with varying environmental conditions such as temperature, day length, and light intensity. Suggested flowering in the northern and western United States is from January through December, but best from mid-March through November. In southern states, year round (January through December), and in Florida, December through April.

The accompanying drawing shows the unique characteristics of the new cultivar, the color being as nearly true as possible with color illustrations of this type.

In the description which follows, color references are to the Munsell Color Book, 1963 edition, and comparisons have been made with the comparison cultivar Neptune.

BOTANICAL CLASSIFICATION

*Chrysanthemum morifolium*

| | Mountain Snow | Neptune |
|---|---|---|
| Bloom: | | |
| Size | 5″ | 4″. |
| Fully expanded | 6½″ | 5″. |
| Borne | Terminal on disbudded branches | Terminal on disbudded branches. |
| Stems | Strong | Strong. |
| Form | Decorative | Decorative. |
| Permanence | 10–12 days | 10–12 days. |
| Color: | | |
| Center of flower | Light green, 2.5GY9/6 to ivory white, 7.5Y9/2 | Streaked pink on white, 2.5RP5/12 with a cool finish of 60° F. or less to white, 7.5Y9/2 at finishing temperatures above this level. |
| Base of petals | Light green, 2.5GY9/6 | White, N9.5/. |
| Inside of petals | White N9.5/ | Do. |
| Reverse of petals | do | Do. |
| Tonality from a distance | White | White. |
| Discoloration | do | White streaked pink, 2.5RP5/12 on N9.5/. |
| Petals: | | |
| Texture | Smooth | Smooth. |
| Appearance and form | Open at base broadening quickly to 1/16″ wide very broad shallow keel. | Slightly open at base. Keeled at mid-point tapering to a point. Several ridges on bottom. 5/16″ wide. |
| Arrangement | Composite, whorled on a single receptacle | Composite, whorled on a single receptacle. |
| Persistence | Resist shatter | Resist shatter. |
| Fragrance | Typical chrysanthemum | Typical chrysanthemum. |
| Reproductive organs: | | |
| Stamen, anthers | None to 30–40 | None to 25–30. |
| Pollen | None to very scant | None to scant. |
| Arrangement | Clustered in center of flower, if present | Clustered in center of flower, if present. |
| Styles | Present both ray and disc florets | Present both ray and disc florets. |
| Length | Short | Short. |
| Ovaries | At the base of petal attached to receptacle | At the base of petal attached to receptacle. |
| Plant: | | |
| Form | Herbaceous | Herbaceous. |
| Growth | Semi-upright | Upright. |
| Height | Approximately 15″ when grown 10 week medium tall treatment as defined in the timetables of Yoder Brothers, Inc. | Approximately 12″ when grown 9 week short treatment as defined in the timetables of Yoder Brothers, Inc. |
| Spread | 8½″ as a pinched plant | 5½″ as a pinched plant. |
| Foliage: | | |
| Top side | Green, 7.5GY3/4 | Very dark green, 5GY2/4. |
| Size | 5″ long, 3″ wide | 4″ long, 2½″ wide. |
| Quantity | Numerous | Numerous. |
| Shape | Spatulate lobed | Spatulate lobed. |
| Texture | Smooth | Smooth. |
| Ribs and veins | Slight prominence | Prominent. |
| Edge | Slightly indented | Indented. |
| Serration | Very slight | Moderate. |
| Underside | Light green, 7.5GY5/4 | Light green, 10GY5/4. |
| Stipules | Very prominent | Prominent. |

We claim:

1. A new and distinct cultivar of chrysanthemum characterized particularly as to uniqueness when compared to the cultivar Neptune, by its 1"–1½" larger flowers, petals approximately ¾" wider, less upright growth habit with about 3" additional spread when comparing single plants, non-pinking of the flower with cool finish of 60° F. or less, lighter foliage, approximately 1" longer leaves, flatter petal during high light, high temperature periods, with no longitudinal roll as the flower matures providing a less aged appearance, greater spread, one week later response, and its 3" more vigor when both grown under the same long day treatment.

No references cited.

ROBERT E. BAGWILL, Primary Examiner